United States Patent [19]

Janata

[11] 4,411,741

[45] Oct. 25, 1983

[54] APPARATUS AND METHOD FOR MEASURING THE CONCENTRATION OF COMPONENTS IN FLUIDS

[75] Inventor: Jiri Janata, Salt Lake City, Utah

[73] Assignee: University of Utah, Salt Lake City, Utah

[21] Appl. No.: 338,943

[22] Filed: Jan. 12, 1982

[51] Int. Cl.³ ............................................ G01N 27/46
[52] U.S. Cl. .................................... 204/1 T; 204/406; 204/411; 204/412; 204/416; 204/431; 324/71.5; 357/25
[58] Field of Search .......................... 357/25; 324/71.5; 204/406, 416, 431, 1 T, 411, 412; 128/635

[56] References Cited

U.S. PATENT DOCUMENTS 3,719,564  3/1973  Lilly, Jr. et al. ..................... 204/415
4,020,830  5/1977  Johnson et al. ...................... 128/635

OTHER PUBLICATIONS

I. Lundstrom et al., "A Hydrogen-Sensitive MOS Field-Effect Transistor," 26 *Applied Physics Letters*, 55–57 (Jan. 15, 1975).

J. H. Griffiths et al., "Applications of the Surface-Potential Detector," *The Chromatography of Gases and Vapours*, Part IV, 3446–3453 (1954).

G. Phillips, "An Electronic Method of Detecting Impurities in the Air," 28 *J. Sci. Inst.* 342–347 (1951).

*Primary Examiner*—G. L. Kaplan
*Attorney, Agent, or Firm*—H. Ross Workman; Allen R. Jensen; Dale E. Hulse

[57] ABSTRACT

An apparatus and method for measuring the concentration of various components in a fluid sample. The apparatus comprises a chemically sensitive field effect transistor (CHEMFET) having a semiconductor substrate and a pair of diffusion regions formed at the surface of the substrate. An electrical insulating layer is positioned adjacent the substrate and a fluid pervious bridge member is mounted to the insulating layer so as to form a gap between the bridge member and insulating layer. The apparatus also includes means for imposing an electrical charge on the bridge member, means for imposing an electrical potential between the diffusion regions, and means for detecting current flow between the diffusion regions. The fluid sample to be analyzed is introduced through the fluid pervious bridge member and into the gap where various components of the fluid sample are adsorbed by the bridge member, and in another embodiment, also by an adsorptive layer which is applied within the gap. The adsorptive layer can be specifically chosen so as to render the apparatus chemically selective of one or more fluid components.

22 Claims, 4 Drawing Figures

APPARATUS AND METHOD FOR MEASURING THE CONCENTRATION OF COMPONENTS IN FLUIDS

BACKGROUND

1. Field of the Invention

The present invention relates to an apparatus and method for measuring the concentration of various components in a fluid, and more particularly, to a field effect transistor which is chemically sensitive.

2. The Prior Art

There have been many different types of field effect transistors (commonly referred to as a "FET") developed for various applications, a few of which are chemically sensitive. Those FETs which are chemically sensitive are often referred to as "CHEMFETs." One type of CHEMFET is an ion-sensitive transistor which was developed for measuring such chemical properties as ion activity and ion concentration in an ion-containing liquid. See, for example, U.S. Pat. No. 4,020,830 entitled "Selective Chemical Sensitive FET Transducers" which issued on May 3, 1977 to Johnson et al., which patent is incorporated herein by reference.

Other electrically sensitive devices have been developed for similar purposes, e.g., a metal oxide semiconductor field effect transistor or "MOSFET" device. See, for example, Piet Bergveld, "Development, Operation, And Application of the Ion-Sensitive Field-Effect Transistor as a Tool For Electrophysiology," *IEEE Transactions of Biomedical Engineering* at 342-51 (September 1972). Although ion-sensitive CHEMFET devices such as those disclosed in U.S. Pat. No. 4,020,830 solve many of the problems experienced by the MOSFET devices disclosed in the above-cited Bergveld article, both of these ion-sensitive CHEMFET and MOSFET devices are limited to the analysis of liquids which are capable of conducting an electrical current.

The need for an apparatus which is capable of measuring the concentration of various components in a nonconducting liquid is readily apparent. For example, it may be desirable to analyze certain liquid petroleum products to determine the amount of impurities contained therein. The prior art ion-sensitive transistors would not be useful for this type of analysis, because a conducting liquid is generally required for the operation of an ion-sensitive transistor and petroleum products are generally nonconductive.

Thus, it will be readily appreciated that what is needed in the art is an apparatus for measuring the concentration of components in a nonconducting liquid. Such an apparatus is embodied in the present invention and serves to complement the prior art by doing what the prior art could not, namely, measure the concentration of components in a nonconducting liquid.

Another limitation of the FET devices known in the art is their limited application in measuring the concentration of impurities and other components in gaseous fluids. Existing devices are generally very specific to the types of gaseous components which can be detected; hence, their versatility is severely limited.

For example, one device has been developed for measuring the concentration of hydrogen in a gaseous sample. (See I. Lundstrom, "A Hydrogen-Sensitive MOS Field-Effecting Transistor," 26 *Applied Physics Letters* 55-57 (Jan. 15, 1975).) This device is a MOSFET which incorporates a palladium layer to absorb and dissolve the hydrogen in the gaseous sample. After absorption and dissolution of the molecular hydrogen gas into the palladium film, the hydrogen molecules dissociate into atomic hydrogen and the dipole moments of the hydrogen atoms cause a change in the work function of the palladium metal. Thus, by measuring the change in the electric potential of such a device, the concentration of hydrogen gas in the sample can be determined.

It will be readily apparent that the above-described hydrogen measuring FET device is limited to detecting only those gaseous components which can penetrate the palladium layer, namely hydrogen. Such a device is obviously not suitable for more general applications of measuring the concentration of other gaseous components.

Another type of device has also been developed which measures the concentration of gaseous components based on changes in the work function of an adsorbing conductor. This device measures the magnitude of the change in work function as the so-called volta potential by a vibrating capacitor. See, for example, G. Phillips, "An Electronic Method of Detecting Impurities in the Air," 28 *J. Sci. Inst.* 342-47 (1951).

Still another type of device which is used for measuring the concentration of various reducible gaseous components is a conductivity measuring apparatus. One such device is disclosed in U.S. Pat. No. 3,719,564. The device disclosed in that patent includes a solidstate electrochemical cell having a pair of electrodes and a rare earth fluoride electrolyte sandwiched therebetween. The concentration of certain reducible gases is measured by exposing the cell to the gaseous sample and recording the cell current which is a function of the concentration of the reducible gases.

Devices such as that described in U.S. Pat. No. 3,719,564 are not only limited to the concentration measurement of reducible gases, but also to those reducible gases which are capable of penetrating the electrolyte material. Thus, any gases which are not capable of sufficiently penetrating the electrolyte go undetected. Moreover, if several reducible gases are present in the gaseous sample analyzed, such a device is incapable of selectively measuring the concentration of each individual gaseous component.

It will thus be appreciated that it would also be an advancement in the art to provide an apparatus which does not require penetration of the gaseous sample into a material within the apparatus so as to render the apparatus capable of measuring the concentration of a variety of different gaseous components, thus providing for general application. It would be a further advancement in the art to provide such an apparatus which could be adapted to selectively measure the concentration of one or more individual gaseous components in a gaseous sample. Such an apparatus and method for measuring the concentration of components in both gaseous and liquid fluids is disclosed and claimed herein.

BRIEF SUMMARY AND OBJECTS OF THE INVENTION

The present invention relates to a CHEMFET apparatus and method for measuring the concentration of various components in both gaseous and liquid fluids. (It should be understood that the term "fluid" as used herein includes both gaseous and liquid fluids.) The apparatus includes a semiconductor substrate which is treated so as to impart a doping polarity to the substrate.

A pair of diffusion regions are formed in the surface of the substrate—one of the regions serving as an electrical source, and the other serving as an electrical drain. The area in the semiconductor substrate between the two diffusion regions defines a conducting channel. An electrical insulating layer is placed adjacent the upper surface of the semiconductor substrate.

A fluid pervious bridge member is mounted to the insulating layer and is made of metal or any other electrically conducting material. The bridge member is curved such that it forms a gap with respect to the insulating layer, and the gap is made accessible to a surrounding fluid environment by means of perforations or holes in the bridge member.

A voltage source is connected to the bridge member and acts to impose an electrical charge on the bridge member. Another voltage source is connected between the drain and source so as to impose an electrical potential therebetween. An ammeter is included in the circuitry so as to detect and measure the drain current. Additionally, a chemically selective adsorptive coating may be applied either to the bridge member or the insulating layer in order to provide for chemical selectivity and to enhance the adsorption of the gaeous components to be analyzed.

In the operation of the novel device and in the implementation of the novel method of the present invention, the fluid to be analyzed is introduced into the gap through the fluid pervious bridge member. Fluid components which have a dipole moment tend to be attracted either to the lower surface of the charged bridge member or to the upper surface of the insulating layer. Those fluid components which are adsorbed at these surfaces will line up so as to modify the electric field within the gap.

The change in the electric field is also felt within the conducting channel, causing the current flow between the source and drain to be either enhanced or impeded. Any change in the current flow between the drain and source is detected and measured by the ammeter; the measured change in current flow in turn provides a means for calculating the concentration of the fluid component adsorbed at the inner surface of the bridge member (that is, the surface of the bridge member adjacent to gap 29).

When a chemically selective adsorptive coating is applied to either the bridge member or the insulating layer, the coating acts to enhance the adsorptive properties of the bridge member. The coating can also be specifically chosen to render the device chemically selective to only certain fluid components.

It is, therefore, an object of the present invention to provide an apparatus and method for measuring the concentration of various components in a nonconducting liquid.

It is another object of the present invention to provide an apparatus and method for measuring the concentration of various components of a gaseous fluid, wherein the apparatus and method do not require penetration of the gaeous components into a material within the apparatus, thereby allowing for the analysis of a variety of different gaseous components.

It is a further object of the present invention to provide an apparatus and method for measuring the concentration of components in a fluid wherein the apparatus and method can be adapted so as to be chemically selective of a certain fluid component.

These and other objects of the present invention will become more fully apparent from the following description taken in conjuction with the accompanying drawings.

DETAILED DESCRIPTION OF THE PREFERRED EMBODIMENTS

Reference is now made to the drawings wherein like parts are designated with like numerals throughout.

Figure 1:
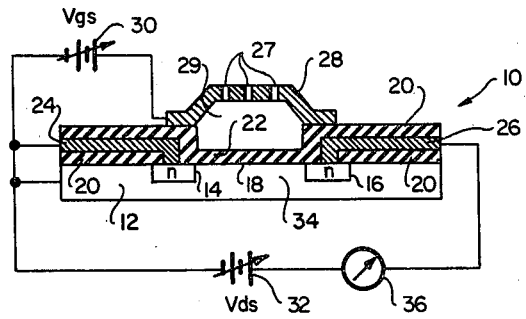
FIG. 1 is a cross-sectional view of one preferred embodiment of the CHEMFET of the present invention.

One preferred embodiment of the chemically sensitive field effect transistor (CHEMFET) of the present invention is generally illustrated at 10 in FIG. 1. Transistor 10 includes a semiconductor substrate 12 which is typically comprised of silicon having a p-type doping plurality. By well-known doping techniques, two spaced-apart diffusion regions 14 and 16 having an n-type doping polarity can be diffused into the surface of substrate 12 to a depth, for example, of from about one to about two microns and spaced about twenty microns apart. One of the n-type diffusion regions is referred to as the source (illustrated as region 14, in FIG. 1) and the other is referred to as the drain (region 16 in FIG. 1).

The surface region of substrate 12 located between the two diffusion regions, and particularly that portion defining the substrate-insulator interface, is commonly referred to as the gate region and is identified herein at 18. Electric insulator material 20 (typically silicon dioxide, silicon nitride, or a silicon dioxide/silicon nitride sandwich) is thermally grown or otherwise deposited on the surface of substrate 12, on portions of diffusion regions 14 and 16, and in particular on gate region 18.

The insulator material between the two diffusion regions is known as gate insulator 22. An electrically conductive material (such as aluminum, n-type silicon, etc.) is deposited on insulator 20 and on the source and drain regions 14 and 16 respectively so as to provide for external electrical contacts 24 and 26 with diffusion regions 14 and 16.

Additional electrically conductive material comprising a bridge member 28 is secured on at least one of its sides to the surface of the insulator material 20 so as to extend over gate region 18 of device 10 so as to form a gap 29 between the lower surface of bridge member 28 and the upper surface of gate insulator 22. Bridge member 28 can be constructed of aluminum, silver, gold, platinum or other electrically conductive materials, including alloys of any of the foregoing. Preferably the gap distance between the lower surface of bridge member 28 and the upper surface of gate insulator is in the range of about 0.5 microns to about 10 microns, with the most presently preferred range being from about 0.1 microns to about 1 micron.

Bridge member 28 is configured so as to be fluid pervious, thereby permitting the passage of liquids and/or gases into or out of the gap 29. The electrically conductive bridge member is typically configured as a grid, mesh, screen, or otherwise perforated plate having apertures 27, so that electricity can be conducted on the bridge member 28 while fluid may simultaneously pass through apertures 27 into gap 29.

Bridge member 28 is additionally coupled to a voltage source 30 which develops a desired reference voltage. A second voltage source 32 is also electrically connected between electrically conductive materials 24 and 26 so as to establish a potential difference between source 14 and drain 16. This potential difference should be of a magnitude sufficient to cause current flow in a conducting channel 34 which is comprised of that portion of the semiconductor substrate 12 which extends between the source and drain diffusion regions 14 and 16, respectively. An ammeter 36 is also coupled in the circuit between the voltage source 32 and the drain region 16 in order to detect and measure the magnitude of the current flow in conducting channel 34, i.e., to measure the magnitude of drain current.

In order to understand the operation and method of the present invention, it is helpful to first consider its functioning in an environment which is free from electrically conductive materials and polar substances. Under these conditions, gap 29 would be filled with an electrically nonconductive material, and this material within the gap would function as an additional electrically insulating layer between bridge member 28 and substrate 12. Thus, when an electrical charge is applied onto bridge member 28 from voltage source 30, a defined electric field is produced between bridge member 28 and the semiconductor substrate 12. If the electrical charge on bridge member 28 is made positive with respect to the charge on source 14, then holes in the substrate 12 are repelled away from the substrate-insulator interface of gate region 18 while electrons are attracted to the interface.

As electron concentrations increase along the interface, the above-described conducting channel 34 is formed between the two diffusion regions 14 and 16. When a potential difference exists between the voltage magnitudes on diffusion regions 14 and 16, the presence of electron concentrations along the substrate-insulator interface of gate region 18 will permit electrical current to flow between these diffusion regions.

The conductance of conducting channel 34, and thus the magnitude of the current flow therethrough, is dependent upon the magnitude of the electrical charge at the interface 18, i.e., upon the potential difference between the bridge member 28 and source duffusion region 14. In other words, the voltage magnitude on bridge member 28 controls the electron density and thus the current flow in conducting channel 34. As a result, the magnitude of the current flow in the conducting channel 34 provides an indication of the magnitude of the voltage on bridge member 28. As discussed in greater detail hereinafter, the ability to relate the magnitude of the current flow in the conducting channel to the voltage magnitude on bridge 28 and to monitor changes therein is an important factor for achieving the surprising results of the present invention.

The magnitude of current flow in conducting channel 34 comprises the drain current ($I_D$) measured at drain 16. The drain current ($I_D$) may be mathematically expressed by the following equation:

$$I_D = \mu_N C_O \frac{W}{L} \left[ V_{gs} - V_{FB} - 2\phi_F + \left(\frac{Q_B}{C_O}\right) V_{ds} - \frac{V_{ds}^2}{2} \right] \quad (1)$$

For $V_{DS} < V_{DSAT}$

Where: $\mu_N$ is the mobility of electrons in the conducting channel 34. $C_O$ is the capacitance of the gate insulator 22. W and L are the width and length of conducting channel 34, respectively; $V_{gs}$ is the magnitude of gate voltage 30; $V_{FB}$ is flat-band voltage; $\phi_F$ is Fermi level of the semiconductor substrante 12; $Q_B$ is the depletion charge in channel 34; $V_{ds}$ is the magnitude of drain to source voltage 32.

The term in equation (1) which is modulated by the adsorption of the dipoles of the fluid components to be detected is $V_{FB}$. This term is defined as:

$$V_{FB} = \phi_M - \phi_S - Q_{ss}/C_O \quad (2)$$

where $\phi_M$ is the work function of bridge member 20; $\phi_S$ is the work function of semiconductor substrate 12; and $Q_{ss}$ is the surface state charge density.

The flat-band voltage ($V_{FB}$) depends on the work function of bridge member 28, which can be expressed as:

$$\phi_M = \mu_e - 4\pi F n \epsilon \cos \alpha \quad (3)$$

where $\mu_e$ is the Fermi level of bridge member 28; F is the Faraday constant; n is the number of adsorbed dipoles ($\epsilon$); and $\alpha$ is the angle of the adsorbed dipoles.

Turning now to the operation of the CHEMFET device as illustrated in FIG. 1, fluids comprising liquids or gases are permitted to pass through apertures 27 in bridge member 28 and to travel into gap 29. If the fluids within gap 29 are purely nonconductive and nonpolar, device 10 will function in the manner described above. However, as polar substances pass into gap 29 between bridge member 28 and insulator 22, the electrical charge emanating from bridge 28 is affected.

More specifically, fluid molecules within gap 29 are attracted to the charged surfaces defining that gap. These fluid molecules which are adsorbed at these surfaces will tend to align themselves such that if a positive charge is present on bridge member 28, the negative terminals of the polar molecules will tend to face bridge member 28 while the positive terminals will generally be directed away from that bridge.

As the concentration of aligend polar molecules increases along the surfaces within gap 29, their dipole moments begin to contribute to the total electric field within gap 29 instead of having a cancelling effect upon each other as is the case with the randomly moving polar molecules within the gap. The net effect of aligning the dipoles of the adsorbed molecules is to increase the positive charge being produced on bridge member 28. Thus, as the positive terminals of the aligned dipoles face toward conducting channel 34, the positive electrical charge present at channel 34 is increased with the result that further holes are repelled from that channel while additional electrons are attracted thereto.

Under the conditions described above, it becomes apparent that the strength of the electric field in the conducting channel 34 is dependent upon both the electrical charge on bridge member 28 and the concentration of aligned dipoles adhering to the surface defining the gap 29. It follows that when voltage source 30 is held constant, the concentration of aligned dipoles adsorbed at the surfaces of the gap 29 controls the magnitude of current flow through conducting channel 34. It is this aligned dipole concentration which controls the magnitude of the drain current. The drain current transmitted from drain region 16 through conductor 26 is measured by ammeter 36 thereby providing a measure of the dipole concentration in the fluid within gap 29.

Of course, it will be recognized that any of the embodiments disclosed herein may be operated as a switching device with the switch position being a function of the current flow through conducting channel 34. Thus, use of ammeter 36 for monitoring this current flow is an optional feature of the invention.

From the above discussion, it becomes apparent that device 10 can be used to measure dipole concentrations in particular regions of a fluid. Thus, for example, device 10 finds particular usefulness in measuring the concentration of a specific component at various locations within a fluid having variable concentrations of that component. The utility of this device will be further appreciated in that, unlike the prior art devices, it may be utilized to analyze both nonconductive liquids and nonconductive gases.

Although the CHEMFET device 10 configured as illustrated in FIG. 1 is subject to use in broad applications, it is also capable of specifically detecting dipoles which comprise a particular substance. This can be accomplished by constructing bridge member 28 of a material which will specifically adsorb that particular substance. Only a slight modification of the device is required to achieve an even greater ability to selectively identify those additional specific fluid components which cannot be adsorbed by bridge member 28. This modification relates to the addition of an adsorptive layer, as set forth in the following discussion of the embodiments illustrated in FIGS. 2 and 3.

Figure 2:
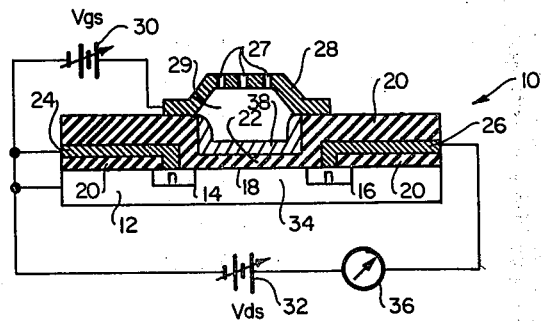
FIG. 2 is a cross-sectional view of a preferred embodiment of the CHEMFET of the present invention, including an adsorptive layer on the upper surface of the insulator in the gap of the invention.

With particular reference to FIG. 2, it is noted that device 10 can be made selective by depositing an adsorptive layer 38 directly onto the upper surface of gate insulator 22. It will be understood that the chemical composition of adsorptive layer 38 will depend upon the fluid components which are to be identified and measured. Any composition which is known to be chemically specific for the adsorption of a certain fluid component can be used in the adsorptive layer to render device 10 chemically specific for that particular component.

For example, it is known that stearic acid will adsorb certain ester compounds. Thus, by constructing adsorptive layer 38 from a material containing stearic acid, a CHEMFET device 10 is provided for detecting and measuring these ester components in the fluid sample.

By way of further example, it is known that some metals (such as silver) act to adsorb hydrogen sulfide ($H_2S$). Thus, by either constructing bridge member 28 of silver, or by constructing adsorptive layer 38 of silver, CHEMFET device 10 is rendered chemically specific for hydrogen sulfide.

It will be appreciated that the foregoing examples for the chemical composition of adsorptive layer 38 are given by way of example only, and that numerous other materials may be used in the construction of adsorptive layer 38 according to the chemical selectivity desired. In choosing an appropriate material for the construction of adsorptive layer 38, the adsorptive properties of the material as well as its degree of specificity for the fluid components sought to be measured should be prime considerations. The known chemical adsorption properties of different materials can be used to construct a variety of devices which are chemically selective for a variety of fluid substances.

From the foregoing, it will be appreciated that the adsorptive layer 28 augments the adsorptive properties of device 10, thus allowing a greater amount of specific components of the fluid substance to accumulate around the lower surface of bridge member 28 and the upper surface of insulating layer 22, which form gap 29. Thus, by modifying device 10 to include adsorptive surfaces, it is possible to identify and measure concentrations of specific components within a given fluid. This feature permits the selective use of device 10 in the analysis of fluids in numerous different types of applications. In addition, any number of devices 10 which have each been made chemically specific for different fluid components can be combined into one unit to provide an apparatus for selectively identifying concentrations of each of the individual components.

Figure 3:
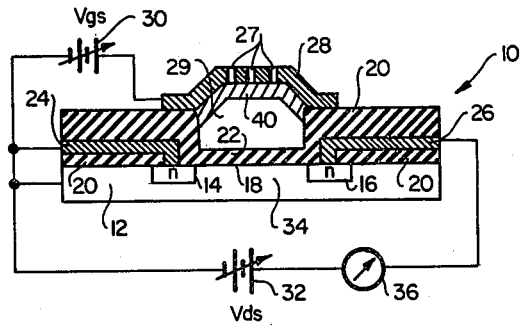
FIG. 3 is a cross-sectional view of a preferred embodiment of the CHEMFET of the present invention illustrating use of an adsorptive layer on the lower surface of the bridge member of this invention.

As an alternative to depositing the adsorptive layer on the insulator 22, FIG. 3 illustrates the deposition of an adsorptive layer 40 onto the lower surface of bridge member 38. Of course, it will be recognized that adsorptive layer 40 must necessarily be configured substantially identical to bridge member 28 so as to permit the free passage of the sample fluid into the gap 29. In all other respects, the device of FIG. 3 is identical in both function and operation to that of FIG. 2.

By means of the above-described selectivity feature, the device as embodied in either of FIG. 2 or 3 can be utilized to identify and measure the concentrations of polar fluids in substantially any gas or substantially any nonconducting liquid. It will also be appreciated that since the embodiments of FIGS. 1-3 of this invention are used in an electrically nonconducting environment, gate insulator 22 can be comprised of the nonconducting fluid within gap 29.

Figure 4:
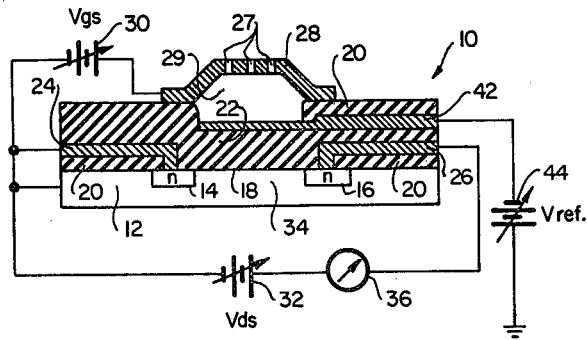
FIG. 4 is a cross-sectional view of another preferred embodiment of the present invention including structure and circuitry which permit use of this embodiment either as a standard MOSFET device, or as a CHEMFET device.

Another preferred embodiment of the CHEMFET device is described by reference to FIG. 4. It will be noted that the device of FIG. 4 is substantially identical to that of FIG. 1 with the exception that a layer 42 of electrically conductive material is deposited upon the upper surface of gate insulator 22 so as to be insulated from contact with substrate 12. Electrically conductive layer 42 extends substantially parallel to the surface of gate region 18 between diffusion regions 14 and 16. Electrically conductive layer 42 is connected at one end to a third voltage source 44 which is itself connected to an electrical reference point, such as ground.

It becomes readily apparent to one skilled in the art that the device of FIG. 4 can be operated as a typical MOSFET device by turning off voltage source 30, and by utilizing voltage source 32 to create a potential between source 14 and drain 16, and by also using voltage source 44 to establish the reference voltage on conductive material 42. Alternatively, with voltage source 44 disconnected and voltage source 30 operating to provide the reference voltage, the device of FIG. 4 will function in a substantially identical manner to the device of FIG. 1. Thus, the embodiment illustrated in FIG. 4 represents a very versatile device which has applications as a typical MOSFET and as a CHEMFET device of the present invention, depending upon the desires of the user.

The device of FIG. 4 may additionally be modified to require only two voltage sources. In one method of accomplishing this, the voltage source 44 is removed and a switch is installed between voltage source 30 and bridge member 28 so as to connect voltage source 30 either to bridge member 28 or to conductive material 42, depending upon the position of the switch. By this means, voltage source 30 may be selectively utilized either as the reference voltage for supplying an electrical charge to bridge 28, or for the reference voltage to supply an electric charge to conductive material 42.

It should also be recognized that the embodiment of FIG. 4 can be rendered more selective toward one or more particular substances by depositing an adsorptive layer upon either the lower surface of bridge member 28 or the upper surface of conductive material 42, in the manner previously described and illustrated with respect to FIGS. 2 and 3. Thus, the device of FIG. 4 is made particularly versatile and useful for numerous applications.

From the foregoing description, it will be appreciated that the novel FET disclosed herein clearly overcomes many of the longstanding problems in the related art by (1) providing a CHEMFET which can be used to analyze nonconducting fluids; (2) providing a CHEMFET which structurally eliminates the need for penetration of a material within the apparatus by a gaseous component to be analyzed; and (3) providing a CHEMFET which is capable of being either general or specific in its application and in its chemical selectivity.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters patent is:

1. An apparatus for detecting a concentration of components in a fluid, comprising:
    a semiconductor substrate having a doping polarity;
    at least two diffusion regions located at a surface of said substrate;
    an electrically insulating layer overlying the surface of said substrate between said diffusion regions;
    a bridge member mounted to said insulating layer so as to form a gap therebetween, said bridge member allowing for passage of fluid into said gap and said bridge member being capable of having an electrical charge imposed upon it;
    means for imposing an electrical charge on said bridge member; and
    means for imposing an electrical potential between said diffusion regions.

2. An apparatus as defined in claim 1 further comprising an adsorptive coating applied to said insulating layer, said adsorptive coating being capable of selectively adsorbing certain components of the fluid.

3. An apparatus as defined in claim 1 further comprising an adsorptive coating applied to said bridge member, said adsorptive coating being capable of selectively adsorbing certain components of the fluid.

4. An apparatus as defined in claim 1 further comprising:
    an electrical conductor positioned adjacent said insulating layer so as to be insulated from said substrate, said conductor being capable of conducting an electrical current; and
    means for imposing an electrical charge on said conductor.

5. An apparatus as defined in claim 4 further comprising an adsorptive coating applied to said conductor, said adsorptive coating being capable of selectively adsorbing certain components of the fluids.

6. An apparatus as defined in claim 4 further comprising an adsorptive coating applied to said bridge member, said adsorptive coating being capable of selectively adsorbing certain components of the fluid.

7. An apparatus as defined in claim 1 wherein a distance between said bridge member and said insulating layer forming said gap is in the range of between about 0.05 microns and about 10 microns.

8. An apparatus as defined in claim 1 wherein a distance between said bridge member and said insulating layer forming said gap is in the range of between about 0.1 microns and about 1 micron.

9. An apparatus as defined in claim 1 further comprising means for detecting current flow between said diffusion regions.

10. An apparatus as defined in claim 1 wherein said bridge member is made of a metal selected from the group consisting of gold, platinum, silver, aluminum, and an alloy of any of the foregoing.

11. An apparatus as defined in claim 1 wherein said insulating layer comprises silicon dioxide.

12. An apparatus as defined in claim 1 wherein said insulating layer comprises silicon nitride.

13. An apparatus as defined in claim 1 wherein said substrate comprises silicon.

14. An improved field effect transistor of the type having a semiconductor substrate with a doping polarity; at least two diffusion regions located at a surface of said substrate; an electrically insulating layer overlying the surface of said substrate between said diffusion regions; an electrically conductive layer overlying the surface of said insulating layer between said diffusion regions; means for imposing an electrical charge on said electrically conductive layer; and means for imposing an electrical potential between said diffusion regions, wherein the improvement comprises:
    a bridge member mounted to the insulating layer and extending over the electrically conductive layer so as to form a gap between said bridge member and said electrically conductive layer, said bridge member allowing for passage of fluid therethrough and being capable of having an electrical charge imposed upon it; and
    means for imposing an electrical charge on the bridge member.

15. An improved field effect transistor as defined in claim 14 wherein the improvement further comprises means for detecting current flow between the diffusion regions.

16. An improved field effect transistor as defined in claim 15 wherein the means for imposing an electrical charge on the electrically conductive layer and the means for imposing an electrical charge on the bridge member comprise a single voltage source selectively connected by a switch means to said electrically conductive layer and to said bridge member.

17. An improved field effect transistor as defined in claim 14 wherein the means for imposing an electrical charge on the electrically conductive layer and the means for imposing an electrical charge on the bridge member comprise a single voltage source selectively connected by a switch means to said electrically conductive layer and to said bridge member.

18. An improved field effect transistor as defined in claim 14 wherein the improvement further comprises an adsorptive coating applied to the electrically conductive layer, said adsorptive coating being capable of selectively adsorbing certain components of the fluid.

19. An improved field effect transistor as defined in claim 14 wherein the improvement further comprises an adsorptive coating applied to the bridge member, said adsorptive coating being capable of selectively adsorbing certain components of the fluid.

20. A method for detecting a concentration of components in a fluid, comprising the steps of:
doping a semiconductor substrate so as to impart a doping polarity to the substrate;
forming at least two diffusion regions at the surface of the substrate;
insulating the surface of the substrate between the diffusion regions by placing an electrical insulating layer adjacent the substrate;
mounting a bridge member to the insulating layer so as to form a gap between the bridge member and the insulating layer;
imposing an electrical charge on the bridge member;
imposing an electrical potential between the diffusion regions;
introducing a fluid through the bridge member and into the gap between the bridge member and the insulating layer; and
detecting current flow between the diffusion regions.

21. A method as defined in claim 20 further comprising the step of applying an adsorptive coating to the insulating layer.

22. A method as defined in claim 20 further comprising the step of applying an adsorptive coating to the bridge member.

* * * * *

UNITED STATES PATENT AND TRADEMARK OFFICE
CERTIFICATE OF CORRECTION

PATENT NO. : 4,411,741
DATED : October 25, 1983
INVENTOR(S) : Jiri Janata

It is certified that error appears in the above—identified patent and that said Letters Patent is hereby corrected as shown below:

Column 1, line 67, "absorb" should be --adsorb--

Column 2, line 1, "absorption" should be --adsorption--

Column 6, line 17, "substrante" should be --substrate--

Column 6, line 56, "aligend" should be --aligned--

Signed and Sealed this

Seventh Day of February 1984

[SEAL]

Attest:

GERALD J. MOSSINGHOFF

Attesting Officer      Commissioner of Patents and Trademarks